(12) United States Patent
Riva

(10) Patent No.: US 9,649,123 B2
(45) Date of Patent: May 16, 2017

(54) DEVICE FOR TREATMENTS WITH ENDOSCOPIC RESECTION/REMOVAL OF TISSUES

(75) Inventor: Raffaele Riva, Lugano (CH)

(73) Assignee: FRII S.A., Luxembourg (LU)

( * ) Notice: Subject to any disclaimer, the term of this patent is extended or adjusted under 35 U.S.C. 154(b) by 0 days.

(21) Appl. No.: 14/128,879

(22) PCT Filed: Jun. 15, 2012

(86) PCT No.: PCT/IB2012/001170
§ 371 (c)(1),
(2), (4) Date: Dec. 23, 2013

(87) PCT Pub. No.: WO2012/176034
PCT Pub. Date: Dec. 27, 2012

(65) Prior Publication Data
US 2014/0155925 A1  Jun. 5, 2014

(30) Foreign Application Priority Data
Jun. 22, 2011  (CH) ...................................... 1058/11

(51) Int. Cl.
*A61B 17/32*  (2006.01)
*A61B 17/16*  (2006.01)
(Continued)

(52) U.S. Cl.
CPC .... *A61B 17/32002* (2013.01); *A61B 17/1622* (2013.01); *A61B 17/1633* (2013.01);
(Continued)

(58) Field of Classification Search
CPC ............................................. A61B 2017/2948
(Continued)

(56) References Cited

U.S. PATENT DOCUMENTS 3,452,741 A   7/1969 Schaffer
3,797,497 A   3/1974 Crim
(Continued)

FOREIGN PATENT DOCUMENTS

DE   10 2006 033439 A1   1/2008
EP       0 700 663 A2    3/1996
(Continued)

OTHER PUBLICATIONS

International Search Report, dated Nov. 14, 2012, from corresponding PCT application.

*Primary Examiner* — Kathleen Holwerda
*Assistant Examiner* — Socrates L Boutsikaris

(57) ABSTRACT

A device for treatments of endoscopic resection/removal of tissues, includes:
a hand-piece;
an outer tubular element extending along a longitudinal axis having a proximal end, a distal end, and a cutting aperture at the distal end;
an inner tubular element housed in rotation in the outer tubular element; the inner tubular element extending along the longitudinal axis and having a proximal end, a distal end and a cutting tip at its distal end;
guiding elements including an electric motor and electric supply to rotate and/or oscillate the inner tubular element with respect to the outer tubular element;
a first engagement keyed substantially at the proximal end of the inner tubular element;
a second engagement keyed on the distal end of the motor's outlet shaft to axially slide thereon; and
at least one spring element to push the second engagement in engagement with the first engagement.

13 Claims, 4 Drawing Sheets

(51) Int. Cl.
  *A61B 17/00* (2006.01)
  *A61B 17/29* (2006.01)
(52) U.S. Cl.
  CPC ......... *A61B 2017/00473* (2013.01); *A61B 2017/00477* (2013.01); *A61B 2017/2927* (2013.01); *A61B 2017/2948* (2013.01); *A61B 2217/005* (2013.01); *A61B 2217/007* (2013.01)
(58) Field of Classification Search
  USPC ......... 606/180, 568, 170–171, 185; 604/272, 604/506; 600/562–568
  See application file for complete search history.

(56) References Cited

U.S. PATENT DOCUMENTS

| | | |
|---|---|---|
| 3,995,619 A | 12/1976 | Glatzer |
| 4,050,528 A | 9/1977 | Foltz et al. |
| 4,649,919 A | 3/1987 | Thimsen et al. |
| 5,490,860 A | 2/1996 | Middle et al. |
| 5,492,527 A * | 2/1996 | Glowa et al. .................. 604/22 |
| 5,505,210 A | 4/1996 | Clement |
| 5,669,921 A | 9/1997 | Berman et al. |
| 5,759,185 A | 6/1998 | Grinberg |
| 5,796,188 A | 8/1998 | Bays |
| 5,849,023 A | 12/1998 | Mericle |
| 5,893,858 A * | 4/1999 | Spitz ............................ 606/170 |
| 6,152,941 A | 11/2000 | Himes et al. |
| 2003/0163134 A1 | 8/2003 | Riedel et al. |
| 2003/0181934 A1* | 9/2003 | Johnston et al. ............. 606/167 |
| 2004/0092992 A1* | 5/2004 | Adams .................. A61B 17/26 606/180 |
| 2005/0159752 A1 | 7/2005 | Walker et al. |
| 2007/0010823 A1 | 1/2007 | Kucklick |
| 2008/0208233 A1 | 8/2008 | Barnes et al. |
| 2008/0234715 A1* | 9/2008 | Pesce .................. A61B 10/025 606/171 |

FOREIGN PATENT DOCUMENTS

| | | |
|---|---|---|
| GB | 2 087 239 A | 5/1982 |
| WO | WO96/29014 | 9/1996 |
| WO | 99/13790 A1 | 3/1999 |
| WO | 03/079911 A1 | 10/2003 |
| WO | 2010/146432 A1 | 12/2010 |

\* cited by examiner

DEVICE FOR TREATMENTS WITH ENDOSCOPIC RESECTION/REMOVAL OF TISSUES

FIELD OF THE INVENTION

The present invention relates to treatments with endoscopic resection/removal of tissues. In particular, the invention relates to an endoscopic device for resection treatments of a soft tissue and of bone tissue (with a relative removal of the fragments produced by such an action).

PRIOR ART

In an alternative to the traditional surgery, which requires a relatively wide cutting in order to access to the surgical site inside the human body, the endoscopic procedures use natural accesses or possibly the formation of small portals (minimal tissue cuttings); therefore it is often referred as endoscopic surgery, with the term of minimally invasive surgery. The two main advantages of the endoscopic surgery are the faster healing of tissues after the surgery and the less exposure of the inner tissues with a risk of infection. The technological developments in this surgical field, also called "closed", have led to the realization of many instruments which are minimally invasive, due to the fact that the access to the surgical site is made through one or more portals. Such instruments must be sufficiently elongated and smooth, in order to permit the entry and its use with a minimal trauma for the surrounding tissues. A portion of the instrument, usually called "distal portion", is designed in order to access to the surgical site; the opposite portion, usually called "proximal portion", remains outside the patient's body. The distal portion of the instrument is usually designed in order to treat the tissue in contact with the same, its shape and size being therefore suitably studied in function of the particular surgical operation to which it is destined.

Nevertheless, the proximal portion is provided with a mechanism for controlling from the outside of the patient's body the aforesaid function. The endoscopic motorized surgical instruments, used in the "closed" surgery, often identified as endoscopic "shavers", are typically made by a pair of coaxial, tubular elements, concentrically placed: an outer element ending in a distal way with an aperture or "cutting window", and an inner rotary element having a cutting surface at the cutting window. The rotary action of the inner, tubular element produces by abrasion the removal or the finishing of the tissue, and this process is called "resection".

As in any other surgical procedure, even in the endoscopic surgery the presence of two well distinct fields is provided: the sterile field, the one in close contact with the patient, in which the surgeon will exerts his procedure, and the one completely separated from the patient and from any object coming in contact with him. To the sterile field only the personnel and duly treated instruments can access (sterilization processes for the instruments, pre-operation washing processes and adoption of protective aids for the personnel, as gloves and surgical gowns); all the elements not coming in contact with the sterile field must strictly remain outside the same.

The Applicant has observed that in the presently existing endoscopic "shavers" and/or in those described before, the inner tubular element is put in rotation and controlled by a handpiece having inside a small electric motor: the activation and the control being made either by buttons placed on the handpiece or by means of buttons placed on a pedal platform. In both cases, the power and the control signal arrive at the handpiece through a wire, connected with an outer console. This "console" is usually placed on a cart sufficiently far from the surgical field, in order not to contaminate the sterile field. The handpiece (in contact with the sterile field) undergoes a sterilisation treatment before any surgical procedure; the console must remain off any contact with the sterile area, and is housed outside aforesaid field; in the presently existing systems, a connecting wire between the handpiece and the "console" is provided. Such connecting wire is treated before any use, in order to make it completely sterile and during the preparation of the surgical procedure it is assembled on the one hand with a (sterile) handpiece and from the other hand the (non sterile) console.

The personnel of the surgery room being in charge of the treatment and management of the instrument must take care, at the end of each operation to wash (with suitable disinfectants and detergents) and then sterilize the re-sterilizable parts (handpiece and wire); washing and sterilization having a negative effect on the useful life of the sterilizable components.

The personnel of the surgery room must also provide for the storage in suitable containers, which guarantee the sterility, with a respective time and space expenditure.

Nonetheless, the personnel of the surgery room must take care of the maintenance of non-sterilizable components, i.e. the console and the possible pedal platform, by providing periodical inspections which can require more complex technical interventions made by the qualified personnel.

In order to solve the aforementioned problems, in the patent application WO2010/146432 by the same Applicant, a device it has been proposed for treatments of endoscopic resection/removal of tissues, providing at least an essential portion of the disposable device. Such portion is represented by the handpiece housing the motor, and by the feeding system, mounted in order to make an integral and non movable body with respect to the same handpiece. In this way, the portion of the device which is more expensive, i.e. the motor, is recovered.

The Applicant has observed instead that in particular for a device as the described one, an engagement between the tang of the blade (tang as inner tubular element) and the motor shaft is necessary, in order to guarantee a simple and precise coupling of the two parts.

The Applicant has also noted that in particular for a device like the one described, it is preferable, in order to obtain a better constructive simplicity, that the motor and in particular its outlet shaft, does not need any markings for coupling with the tang of the blade.

SUMMARY OF THE INVENTION

The Applicant has noted that with a device for treatments with endoscopic resection/removal of tissues providing a first engagement, which is keyed on the tubular element, a second engagement which is keyed on the distal end of the outlet shaft of the motor and at least one spring element in order to push said second element in engagement with said first engagement, is possible to obtain a simple and precise coupling of the two engagements and also, differently from the existing devices, the motor and in particular its outlet shaft do not need any reference for coupling with the tang of the blade. In one of his aspect, the invention relates to a device for treatments with endoscopic resection/removal of tissues, comprising:

a handpiece, able to be handled by a user;

an outer tubular element, extending along a longitudinal axis (X-X) and comprising a proximal end, a distal end and a cutting aperture, placed at said distal end;

an inner tubular element, able to be housed in a rotary way in said outer tubular element; said inner tubular element extending along a longitudinal axis (X-X) and comprising a proximal end, a distal end and a cutting tip at its distal end;

guiding means in order to put in rotation and/or oscillation said inner tubular element with respect to said outer tubular element; said guiding means comprising an electric motor and electric feeding means for said electric motor;

characterized in that it comprises:

a first engagement, keyed on the inner tubular element, substantially at the proximal end of the inner tubular element;

a second engagement, keyed on the distal end of the outlet shaft of the motor, in order to axially slide on the outlet shaft of the motor;

said second engagement being shaped in order to couple with said first engagement, and to drag said inner tubular element; and at least one spring element, in order to push said second engagement in a coupling with said first engagement.

The present invention, in the aforementioned aspect, can have at least one of the preferred properties, described here in the following.

The first engagement comprises a first toothed gear comprising a plurality of teeth distanced along a circumference, in order to form a plurality of seats.

Preferably, the device comprises at least one blocking ring, to associate the outer and inner tubular elements to the hand-piece, and in particular in its distal portion.

Advantageously, the second engagement comprises a toothed gear, comprising a plurality of teeth distanced along a circumference, and able to engage with the seats of the first toothed gear.

Preferably, the device comprises a keyed support element and fixed by fixing means to the outlet shaft of the motor, the support element being able to drag in a rotary way said second engagement.

Conveniently, the spring means comprise a spring, which is mounted in a concentric way on the outlet shaft of the motor and interposed between the second engagement and the support element, in order to exert a pressure in a longitudinal direction, over the second engagement.

Preferably, the device for treatments with endoscopic resection/removal of tissues comprises a final stroke element of the axial sliding of the second engagement, said final stroke element being mounted on the end of said outlet shaft of the motor, in a distal way with respect to the second engagement.

Conveniently, the device for treatments with endoscopic resection/removal of tissues comprises a front tight element in order to protect said guiding means from the pollution of suction liquids.

Advantageously, an orientating organ is present, in order to orientate in at least three angular positions the outer tubular element, with respect to the inner tubular element.

Preferably, the orientating device comprises at least one stopping tooth, to be integral with the outer tubular element, and able to engage with at least three radial seats, realized in the handpiece.

Advantageously, the device comprises a cooling circuit, comprising a link for a suction assembly, at least one duct, directing the cooling flow to said inner tubular element and a device for regulating the suction.

Preferably, the duct which direct the cooling flow to the inner tubular element extends in a longitudinal direction along the handpiece, and it has a substantially elongated section, in a direction perpendicular to the longitudinal axis (X-X).

Advantageously, a transmitting assembly of the motion, actuated by said electric motor, is present, in order to rotate said inner tubular element with respect to said outer tubular element.

Advantageously, the guiding means are contained inside a body, which can be inserted without moving into the handpiece.

Preferably, the body is water-tight.

In order to permit an easy and rapid extraction of the guiding means, with respect to the handpiece, said handpiece can comprise a distal portion, which supports the outer tubular element and the inner tubular element and a proximal portion, which can be coupled without moving to the distal portion.

Advantageously, the guiding means comprise a control unit container into said body.

The control unit can comprise at least one electronic circuit, in order to regulate the functions and the speed of the electric motor, and a plurality of buttons, placed on the outer surface of said guiding means, in a position corresponding to buttons of a flexible material, provided on the outer surface of the handpiece.

Advantageously, the suction and cooling circuit has a portion with a thermal exchange to said electric motor, in order to retain the heating of the electric motor.

Preferably, the device for regulating the suction comprises a tap and a lever, in order to control the tap from the outside.

Advantageously, the electric motor is a brushless motor.

BRIEF DESCRIPTION OF THE DRAWINGS

Further properties and advantages of the invention will be clearer from the detailed description of some preferred but not exclusive embodiments, of a device for treatments with endoscopic resection/removal of tissues, according to the present invention.

Such a description will be explained below, with reference to the annexed drawings, given for an indicative aim only, and therefore for a non limiting aim, wherein.

DETAILED DESCRIPTION OF EMBODIMENTS OF THE INVENTION

Figure 1:
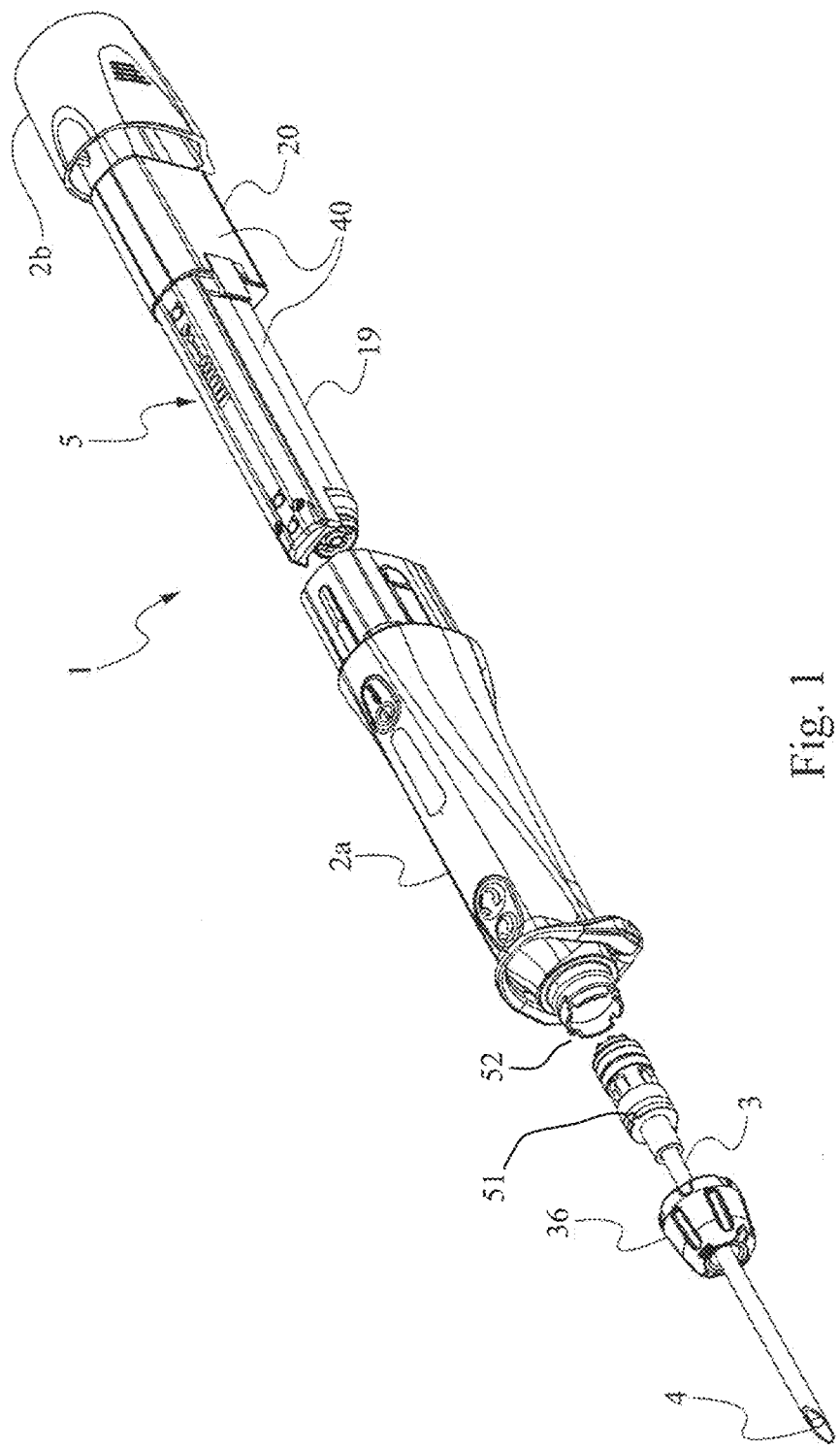
FIG. 1 is a schematic exploded view of a preferred embodiment for realizing the device for treatments of endoscopic resection/removal of tissues, according to the present invention.

With reference to FIGS. 1-4, a device for treatments of endoscopic resection/removal of tissues is indicated with the reference number 1.

The device for treatments of endoscopic resection/removal of tissues 1 comprises a handpiece 2 able to be handled by a user, an outer tubular element 3, an inner tubular element 4 and guiding means 5 in order to rotate and/or oscillate the inner tubular element 4 with respect to the outer tubular element 3.

The outer tubular element 3 extends along a longitudinal axis X-X and it comprises a proximal end, a distal end and an aperture and/or cutting window, placed at its distal end.

The inner tubular element 4 is shaped and sized in order to be housed in a rotary way in the outer tubular element 3 and it also extends along the longitudinal axis X-X. The inner tubular element 4 comprises a proximal end, a distal end and a cutting tip, at its distal end, in order to face the cutting window. The rotary action of the inner tubular element 4 produces by abrasion the removal or finishing of the tissue, and this process is defined as "resection".

The guiding means 5 comprise an electric motor 19 and electric supply means 20 for the electric motor 19. In a preferred embodiment, the guiding means 5 can be used again, whereas the handpiece is disposable or single-used. For such an aim, the guiding means 5 are housed into a suitable body 40 which can be completely housed into the handpiece 2. In this way, the portion of device which is more expensive can be recovered.

In order to permit an easy and rapid extraction of the guiding means 5 and in particular of the body 40 with respect to the handpiece 2, said hand-piece 2 can comprise a distal portion 2a supporting, as it is explained in greater detail below, the outer tubular element 3 and the inner tubular element 4 and a proximal portion 2b which can be coupled without moving to the distal portion 2a.

The electric motor 19, is preferably a motor of the brushless type, but another type of electric motor of suitable sizes and similar power could also be used for such an aim. The motor 19 is able to rotate at a speed comprised between 400 and 6000 revolutions per minute.

The electric motor 19 is controlled by a control unit, which controls all the functions of the device 1, as to say the turning on, the rotation or the simple oscillation of the inner tubular element 4 with respect to the outer tubular element 3, and the rotary speed of the inner tubular element 4.

The control unit is also provided in the body 40.

The control unit comprises at least one main electronic circuit, supported by an electronic circuit of the support and by an auxiliary electronic circuit.

The main electronic circuit is connected to buttons, which permit to choose from the outside the kind of instruction to be sent to the main electronic circuit, as to say the turning off of the device 1, the kind of oscillation/rotation of the inner tubular element.

Figure 2:
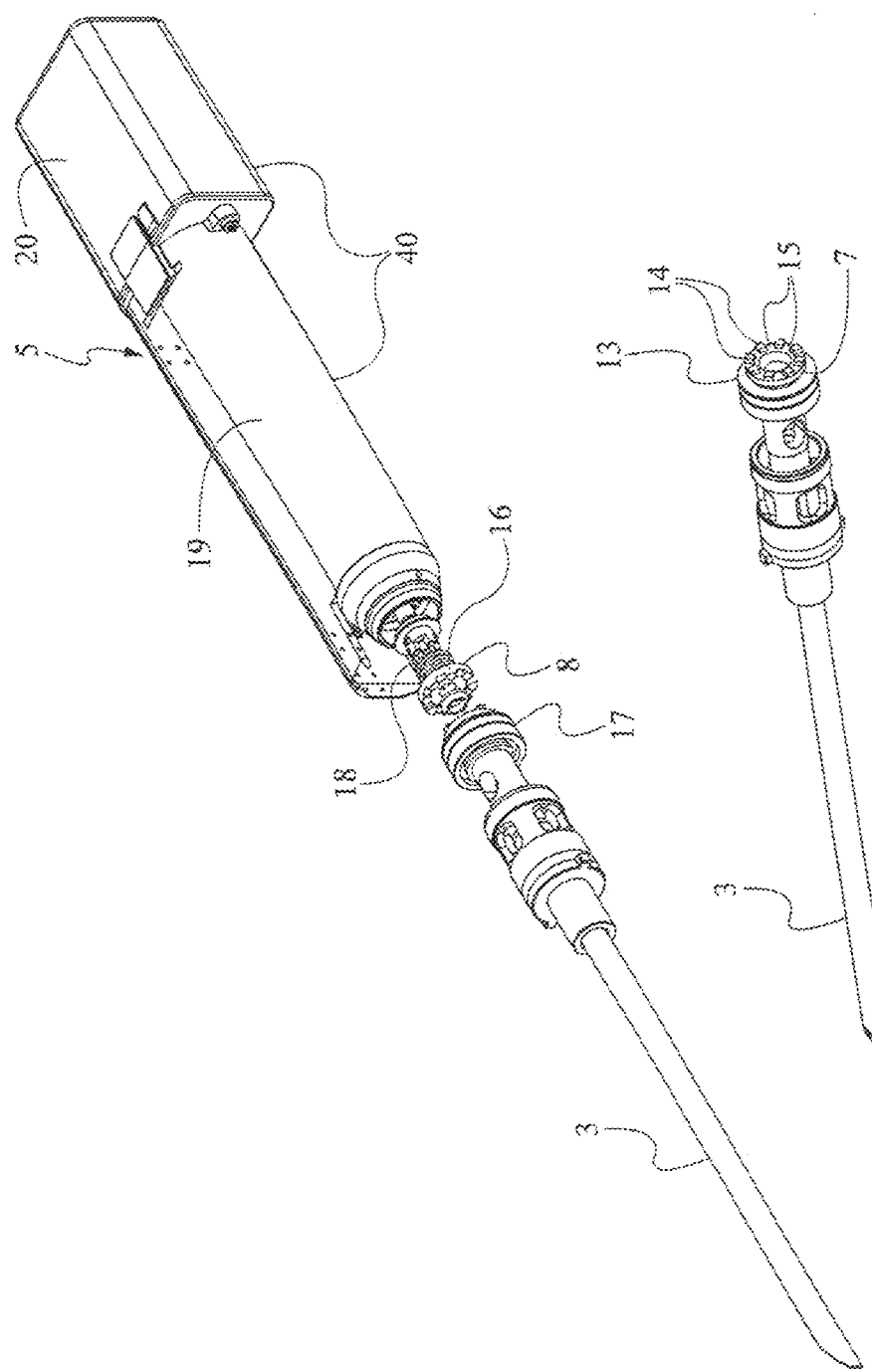
FIG. 2 is a schematic exploded view of an inner portion of the device for treatments of endoscopic resection/removal of tissues, shown in FIG. 1.
Figure 3:
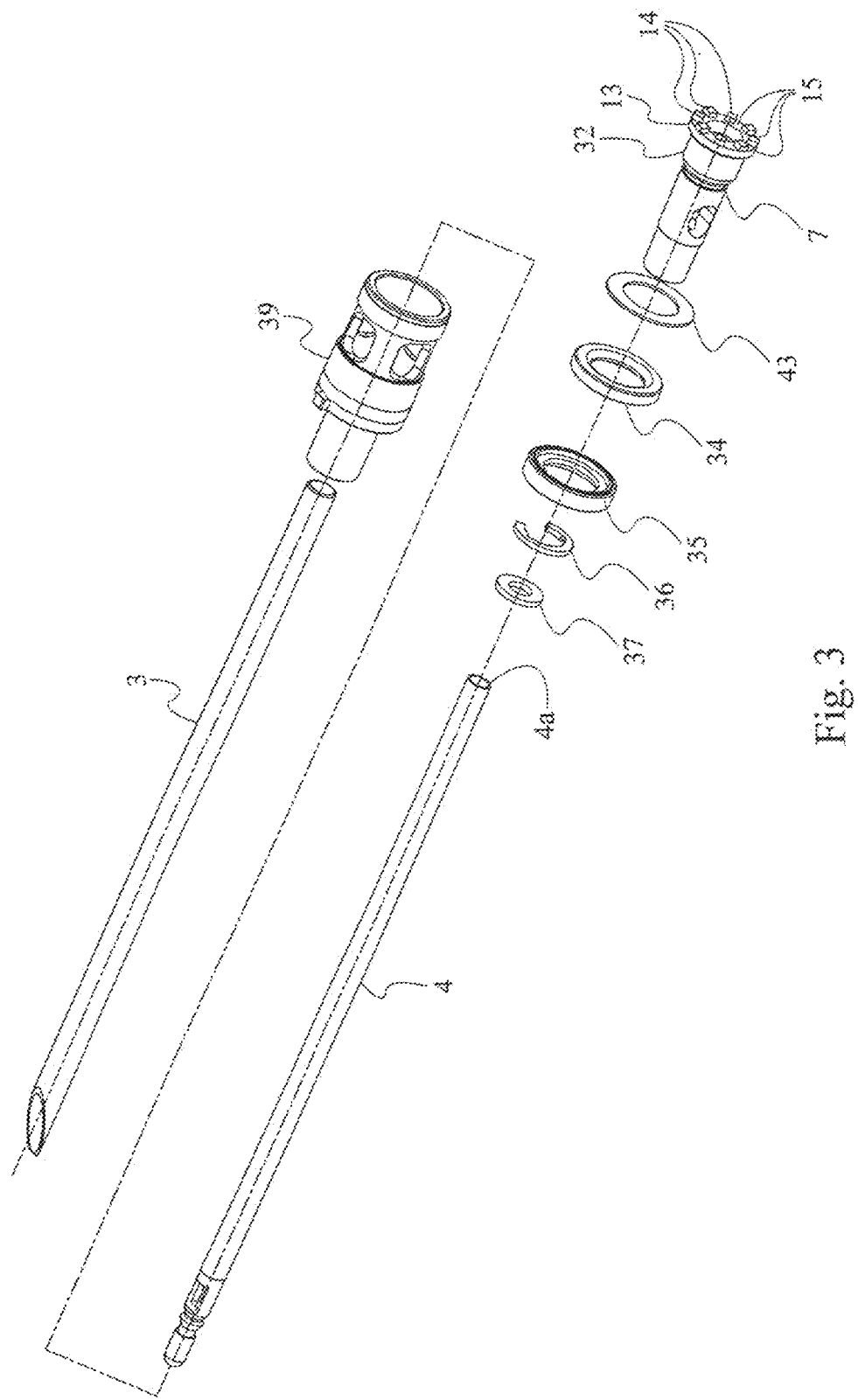
FIG. 3 is a schematic exploded view of the distal portion of the device in FIG. 1.

The electric supply means 20 of the preferred embodiment, shown in FIGS. 1-3 are represented by alcalyne or lithium, rechargeable batteries, but any other type of batteries could also be used for such an aim, without departing from the protective field of the present invention.

The batteries are contained into a container 23 provided at the more proximal end of the body.

The container 23 has electric connections suitable to supply the electric motor 19 and a non movable cover for substituting batteries and for detecting the electric connections.

Preferably, the container 23 is also water-tight.

The electric motor 19 is housed in the body 40 which axially extends into the handpiece 2.

The body 40 centrally houses the motor pinion, in a proximal position the control unit which controls and detects the motor 19 and frontally the motion transmission assembly.

As can be seen in FIG. 1, the outer tubular element 3 through a blocking ring 36 is linked to the handpiece 2, and in particular to its distal portion 2a.

Inside the body 40 a motion transmission assembly is also present, comprising a satellite reducer.

In detail, the inner tubular element 4 is brought by an outlet shaft 17 of the motor which, through a motor pinion, connects in a functional way the inner tubular element with the electric motor 19.

Between the motor pinion and the outlet shaft 17 of the motor is also provided a box for the satellite reducer, comprising the satellites and the satellite support shaft.

The transmission assembly of the motion also has two radially interposed supports, between the outlet shaft 17 of the motor and the box per the satellite reducer.

The motor pinion engages on the satellites, which through the satellite support shaft transfer the motion to the outlet shaft 17 of the motor.

Alternatively to the now described coaxial transmission assembly, a transmission assembly can be provided, with a gear chain which has the outlet shaft 17 functionally connected with a motor pinion to the electric motor 19.

In this case, nevertheless, between the outlet shaft 17 first reduction pinions, a rotary pin of the first reduction pinions and flattening washers could be provided.

The outlet shaft 17 of the motor could be supported in a rotary way by a bearing and by a bushing, placed at the axially distal end of the outlet shaft 17 of the motor.

According to a relevant aspect of the present invention the device 1 comprises a first engagement 7 on the inner tubular element 4 at its proximal end 4a, a second engagement 8 on the distal end 17b of the outlet shaft 17 of the electric motor in order to axially slide on the outlet shaft 17 of the electric motor and at least one spring element 18 in order to bring the second engagement 8 in an engagement with said first engagement 7.

The second engagement 8 is shaped in order to couple with the first engagement 7, in order to drag in a rotary way the inner tubular element 4.

In particular, the first engagement 7, in the embodiment shown in FIGS. 2 and 3, has a first toothed gear 13 comprising a plurality of teeth 14 distanced along a circumference, in order to form a plurality of seats 15.

Preferably, as in the embodiment shown in the figures, eight seats 15 and eight teeth 14, at a mutual distance are present.

The toothed gear 13 is realized in a plastic material, keyed and fixed with a hot treatment on the inner tubular element 4.

The first engagement 7 also comprises a bushing 32, in stainless steel, a tight element 34, and a locking ring 35 which keeps in position the first engagement 7 and consequently the inner tubular element 4 with respect to the handpiece 2, being mounted with an interference to the inner diameter of the handpiece 2.

The front tight element 34 protects the guiding means 5, as to say the electric motor 19 and the supply element 20, mounted in the body 40, from the pollution of the supplying liquids.

The front tight element 34 avoids the supply liquids passing into the inner tubular element 4, by being kept in contact with the body 40 and with the guiding means 5 contained in that the body.

Preferably, the first engagement 7 also has a flattening bushing 43, a locking ring of the "seeger" type 36 and a locking bushing 37, which avoids the movement in a longitudinal direction, along the axis X-X of the inner tubular element 4.

On the outer tubular element 3, as better shown in FIG. 3, an outer guiding element 39 is present, to be realized preferably in a plastic material, able to couple and to be concentrically mounted on the bushing 32.

The outer guiding element 39 is keyed in a fixed way, preferably with a hot treatment, on the outer tubular element 3.

The outer guiding element 39 also realizes a partially orientating device, in at least three angular positions, of the outer tubular element 3 with respect to the inner tubular element 4, as will be described in more detail in the following.

Analogously the first engagement 7, the second engagement 8 comprises a second toothed gear 16 also having a plurality of teeth 29 distanced along a circumference, shaped and dimensioned in order to engage with the seats 15 of the first toothed gear 13.

The teeth 29 are in turn distanced along a circumference, in order to form a plurality of seats 28 able to house and engage the teeth 14 of the first toothed gear 13.

Preferably, as in the embodiment shown in the figures, eight seats 28 and eight teeth 29 are present, at a mutual distance.

Figure 4:
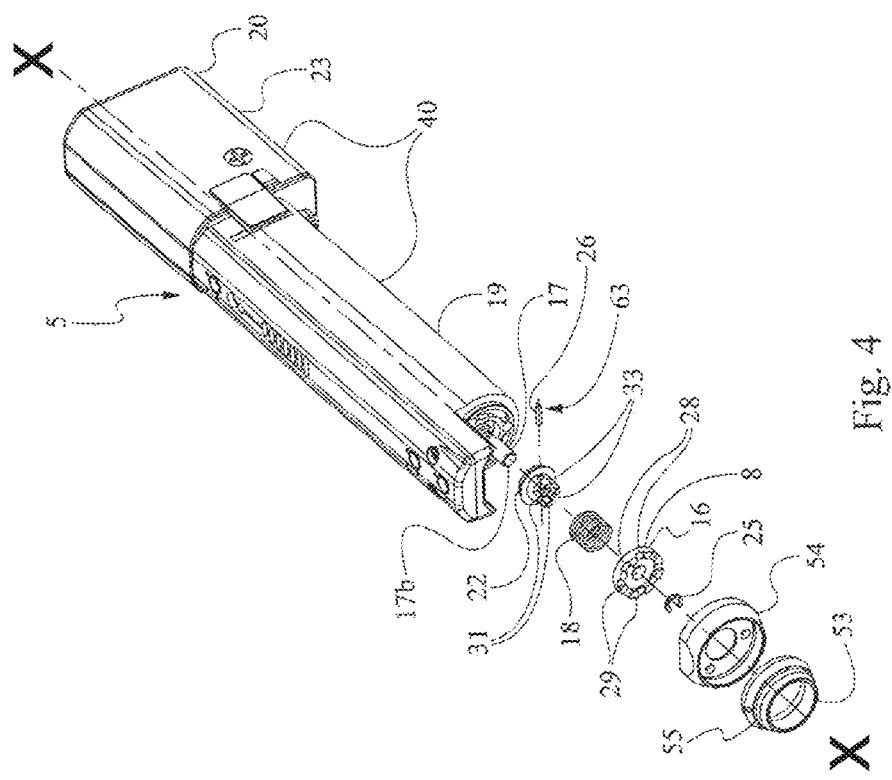
FIG. 4 is a schematic exploded view of the proximal portion of the device in FIG. 1.

With reference to the embodiment shown in FIG. 4, upwards of the first engagement 7 in a longitudinal direction, underlined with the axis X-X, a support element 22 is present, keyed and fixed to the outlet shaft 17 of the motor.

The support element 22 is able to drag in a rotary way the second engagement 8 and it is fixed to the outlet shaft 17 of the motor, through suitable fixing means 63, such as for example a pin 26 able to enter in a suitable seat obtained on the outlet shaft 17 of the motor.

In order to drag in a rotary way the second engagement 8, the support element 22 has four front teeth 31, circumferentially distanced in order to form four seats 33 able to engage with four teeth, not shown in said figure, and provided for such an aim on the second engagement 8 and facing the support element 22.

The second engagement 8 has, in fact, four little teeth, circumferentially spaced in order to form respective seats, also not shown in said figure. The little teeth are able to engage with the seats 33 of the support element 22 whereas four seats of the second engagement 8 are sized and shaped in order to engage with the four front teeth 31 of the support element 22. When the device 1 is assembled and mounted the four front teeth 31, respectively the four seats 33, of the support element 22 are in engagement with the respective seats, such as little teeth, of the second engagement 8. Such an engagement is substantially free from circumferential grooves in order to avoid "snap" movements during the inverting of the rotary direction of the outlet shaft 17 of the motor.

The spring elements 18 comprise a spring, preferably with an helical shape, concentrically mounted on the outlet shaft 17 of the motor and interposed between the second engagement 8 and the support element 22, in order to exert a pushing movement in the longitudinal direction, on the second engagement 8.

During the assembling of the device 1, the spring means 18 push the second engagement 8 towards the first engagement 7, in order to permit the mutual engagement between the teeth 14 and the seats 15 of the first engagement 7 and the little teeth 29 and the seats 28 of the second engagement.

In the case a perfect engagement between the teeth 14 and the seats 15 of the first engagement 7 and the little teeth 29 with seats 28 of the second engagement 8 do not happen, when the motor 19 is actuated, the second engagement tends to move in the longitudinal direction towards the proximal portion of the handpiece 2 and to return immediately towards the distal direction, pushed by the spring means 8, until an engagement between teeth 14 and seats 15 of the first engagement 7 and the little teeth 29 and the seats 28 of the second engagement 8 is not found.

The aforesaid operation requires only fractions of seconds, and it is more rapid with the increase of the number of teeth and of seats of the two engagements 7 and 8.

In order to stop the sliding in the longitudinal direction of the second engagement 8, along the outlet shaft 17 of the motor, a final stroke element 25 is present.

The final stroke element 25, represented by a "seeger" type ring, is mounted on the end of the outlet shaft 17 of the motor, distally with respect to the second engagement 8.

In FIG. 4, two protective conical elements 53,54 are shown, preferably made of aluminium.

In detail, the conical ring 54 is mounted on the body 40 and the conical ring 53 is directed by means of a thread not shown on the conical ring 54.

The conical rings 53,54 protect the engagement from the outside and avoid that anyone could accidentally arrive to the engagement 8 during its operation.

Preferably, on the conical ring 53, in one of its suitable groove, a second tight element 55 is provided, such as o-ring in rubber, in order to protect the guiding means 5 from the pollution of the suction liquids, in case of a failure of the first front tight element 34.

As previously cited, according to an advantageous aspect of the present invention, the outer guiding element 39 also partially realizes an orientating element, to orientate in at least three angular positions the outer tubular element 3 with respect to the inner tubular element 4.

For such an aim, the outer guiding element has two little teeth 51 which radially projects and with a diametrical space on the outer periphery of the outer guiding element 39.

The little teeth 51 are able to engage in suitable seats 52, realized on the end of the distal portion 2a of the hand-piece 2.

In detail, four seats 52, circumferentially distanced are present, with an arch of ¼ circumference.

By varying the engagement of the little teeth 51 with the seats 52, the outer tubular element 3 is angularly rotated of around 90° and so its cutting window.

In such a way, for the surgeon, some particular operations do not require anymore the rotation of the hand in un easy positions, but the simple rotation of the cutting window of the outer tubular element 3, with a possible choose among four angular positions.

Preferably, the device 1 according to the present invention can comprise a suction and cooling comprising a linking 9 for a suction apparel, external to the handpiece 2 and not shown in the figures, at least one duct that said linking 9 directs the cooling fluid to the inner tubular element 4 and a device for regulating the supply of the cooling fluid to the inner tubular element.

The supply for regulating the cooling fluid to the inner tubular element comprises a tap 14 and a lever 13 in order to control from the outside the tap 14. Advantageously, the cooling circuit has an exchanging portion of thermal heating with said electric motor 19 in order to retain the heating.

To achieve such an aim, the portion of heat exchange function happens inside the hand-piece 1, longitudinally along the axis x-x, in order to extend the heat exchange function, in an axially way, all the way to the motor 19.

Advantageously, the portion of heat exchange is represented by a section of the duct which, from the connection 9 directs the cooling fluid to the inner tubular element 4, such duct section having a substantially elongated cross-section, in the perpendicular direction with respect to the longitudinal axis (X-X).

Preferably, said duct has an elliptical cross-section.

The aforementioned design permits both increasing the efficiency of heat exchange and and reducing the impact of such a portion on the ergonomy of the handpiece 2.

According to an advantageous aspect of the present invention, the hand-piece 2 is water-tight.

The present invention has been described with reference to some operative embodiments. Several changes can be made to the operative embodiments, described in detail, by remaining in any case in the protection field of the invention, defined by the following claims.

The invention claimed is:

1. A device for treatments of endoscopic resection/removal of tissues, comprising:
    a handpiece able to be handled by a user and having a longitudinal axis, the handpiece having a distal end and a proximal end;
    a guide member comprising a body housing a battery-powered electric motor and a battery connected to power said electric motor,
    the body being removably housed within the handpiece by insertion into, and removal from, the proximal end of the handpiece;
    an outer tubular element removably coupled to the distal end of the handpiece and extending along the longitudinal axis of the handpiece, the outer tubular element having a proximal end, a distal end, and a cutting aperture located at said distal end of the outer tubular element;
    an inner tubular element housed in, and rotatable with respect to said outer tubular element, said inner tubular element extending along the longitudinal axis of the handpiece and including a proximal end, a distal end, and a cutting tip at said distal end of the inner tubular element, the cutting tip facing the cutting aperture;
    the electric motor being configured to cause said inner tubular element to at least one of rotate and oscillate with respect to said outer tubular element, the electric motor having an outlet shaft extending from the distal end of the handpiece, wherein the electric motor provides rotary action of the inner tubular element to produce, by abrasion, removal or finishing of tissue to thereby effect resection;
    a first engagement mounted on the inner tubular element substantially at the proximal end of the inner tubular element;
    a locking element that maintains the first engagement and the inner tubular element in a fixed longitudinal position with respect to the handpiece, the locking element directly circumferentially surrounding the first engagement and being mounted such that an outer surface of the locking element is conterminous with an inner surface of an inner diameter of the handpiece;
    a second engagement mounted directly on an outermost location of a distal end of the outlet shaft of the electric motor and directly circumferentially surrounding an outer surface of said outlet shaft to longitudinally slide on the outlet shaft of the electric motor;
    said second engagement shaped to couple directly with said first engagement, and to drag, in a rotary way, said inner tubular element; and
    at least one spring element that directly contacts and pushes said second engagement into direct engagement with said first engagement by causing said second engagement to slide directly on said outer surface of said outlet shaft, to thereby couple the outlet shaft of the electric motor with the inner tubular element to have the electric motor at least one of rotate and oscillate the inner tubular element with respect to the outer tubular element.

2. The device according to claim 1, wherein said first engagement comprises a first toothed gear comprising a plurality of teeth spaced along a circumference, to form a plurality of seats.

3. The device according to claim 2, wherein said second engagement comprises a second toothed gear comprising a plurality of teeth spaced along a circumference, the teeth of the second toothed gear engaging with the seats of the first toothed gear to have the electric motor cause the inner tubular element to rotate with respect to the outer tubular element.

4. The device according to claim 1, further comprising a support element mounted on and fixed to said outlet shaft of the electric motor, said support element being able to drag, in a rotary way, said second engagement.

5. The device according to claim 4, wherein said at least one spring element comprises a spring, concentrically mounted on the outlet shaft of the electric motor, and interposed between said second engagement and said support element in order to exert a push in a longitudinal direction on said second engagement.

6. The device according to claim 1, further comprising a final stroke element for the longitudinal sliding of said second engagement, said final stroke element being mounted on a top of said outlet shaft of the electric motor, in a distal way with respect to the second engagement.

7. The device according to claim 1, further comprising at least one front tight element to protect said guide member from pollution by suction liquids.

8. The device according to claim 1, further comprising an orientating device to orientate, in at least three angular positions, the outer tubular element with respect to the handpiece.

9. The device according to claim 8, characterized in that said orientating device comprises at least one stopping tooth integral with the outer tubular element able to engage in at least three seats, radially spaced and made on the handpiece.

10. The device according to claim 1, wherein the battery comprises removable batteries located within a container having electric connections that supply electricity from the batteries to the electric motor, the container located at a proximal end of the body.

11. The device according to claim 1, wherein the electric motor oscillates said inner tubular element with respect to said outer tubular element.

12. The device according to claim 3, further comprising a support element mounted on and fixed to said outlet shaft of the electric motor, said support element having teeth facing a distal end of the device, the teeth of the support element circumferentially distanced to provide seats, and with the teeth of the support element engaging the second engagement, the support element drags, in a rotary way, said second engagement.

13. The device according to claim 12, wherein said at least one spring element comprises a spring, concentrically mounted on the outlet shaft of the electric motor, and interposed between said second engagement and said support element in order to exert a push in a longitudinal direction on said second engagement towards the first engagement in order to permit mutual engagement between the teeth and the seats of the first engagement and the teeth and the seats of the second engagement.

\* \* \* \* \*